US012728106B2

(12) United States Patent
Daud et al.

(10) Patent No.: US 12,728,106 B2
(45) Date of Patent: Sep. 8, 2026

(54) MULTIPARTICULATE PHARMACEUTICAL COMPOSITION OF TAMSULOSIN AND SOLIFENACIN

(71) Applicant: Zim Laboratories Limited, Maharashtra (IN)

(72) Inventors: Anwar Daud, Maharashtra (IN); Chandrashekhar Mainde, Maharashtra (IN); Anil Jadhav, Maharashtra (IN); Yuvraj Rathod, Maharashtra (IN); Uttam Kedar, Maharashtra (IN)

(73) Assignee: Zim Laboratories Limited, Maharashtra (IN)

( * ) Notice: Subject to any disclaimer, the term of this patent is extended or adjusted under 35 U.S.C. 154(b) by 552 days.

(21) Appl. No.: 17/920,200

(22) PCT Filed: Apr. 26, 2021

(86) PCT No.: PCT/IB2021/053415
§ 371 (c)(1),
(2) Date: Oct. 20, 2022

(87) PCT Pub. No.: WO2021/220133
PCT Pub. Date: Nov. 4, 2021

(65) Prior Publication Data

US 2023/0248673 A1 Aug. 10, 2023

(30) Foreign Application Priority Data

Apr. 27, 2020 (IN) ............................ 202021017897

(51) Int. Cl.
*A61K 31/18* (2006.01)
*A61K 9/20* (2006.01)
*A61K 31/4725* (2006.01)

(52) U.S. Cl.
CPC ............ *A61K 31/18* (2013.01); *A61K 9/2027* (2013.01); *A61K 9/2095* (2013.01); *A61K 31/4725* (2013.01)

(58) Field of Classification Search
CPC .... A61K 31/18; A61K 9/2027; A61K 9/2095; A61K 31/4725; A61K 9/0053; A61K 9/10; A61K 9/167; A61K 9/4858; A61K 9/5073; A61K 9/0095
See application file for complete search history.

(56) References Cited

U.S. PATENT DOCUMENTS

| | | | | |
|---|---|---|---|---|
| 4,576,646 | A * | 3/1986 | Branco | A61K 9/2866 106/162.7 |
| 9,198,904 | B2 * | 12/2015 | Yasuji | A61K 31/439 |
| 2007/0270459 | A1 * | 11/2007 | Van Meeteren | A61K 31/18 514/307 |
| 2008/0103171 | A1 | 5/2008 | Umejima et al. | |
| 2019/0167612 | A1 | 6/2019 | Kim et al. | |

FOREIGN PATENT DOCUMENTS

| | | | |
|---|---|---|---|
| CN | 106562968 | A * | 4/2017 |
| EP | 2394648 | A1 | 12/2011 |
| WO | WO-2006/070735 | A1 | 7/2006 |
| WO | WO-2010/136193 | A1 | 12/2010 |
| WO | WO-2019/013403 | A1 | 1/2019 |
| WO | WO-2019/076966 | A1 | 4/2019 |

OTHER PUBLICATIONS

Anonymous. Ataman Chemicals [online]; 2015; downloaded from <URL https://atamankimya.com/sayfalar.asp?LanguageID=2&cid=3&id=978&id2=11860 > on Apr. 19, 2025; 8 pages. (Year: 2015).*
International Search Report and Written Opinion for PCT/IB2021/053415, dated Aug. 19, 2021, 9 pgs.
M. Romancik et al., "Tamsulosin/Solifenacin Fixed-Dose Combination Tablet for the Treatment of Male Lower Urinary Tract Symptoms", Drugs Today (Barc), 2014, 50(12):803-11.doi:10.1358/dot.2014.50.12.2247444, 1 page.

* cited by examiner

*Primary Examiner* — David Browe
(74) *Attorney, Agent, or Firm* — BLANK ROME LLP

(57) ABSTRACT

The present disclosure relates to a multiparticulate and multilayered composition. The inner layer has tamsulosin or a pharmaceutically acceptable salt thereof in a modified release form. The outer layer has solifenacin or a pharmaceutically acceptable salt there of in an immediate release form. There are one or more protective layers configured to protect the outer layer. The composition also contains pharmaceutically acceptable excipients. The composition has a plurality of discrete or aggregated particles irrespective of their size, shape or morphology, and releases the drug at a predetermined rate.

14 Claims, No Drawings

MULTIPARTICULATE PHARMACEUTICAL COMPOSITION OF TAMSULOSIN AND SOLIFENACIN

This application is a national stage of International Application No. PCT/IB2021/053415, filed on Apr. 26, 2021, which claims priority to Indian Patent Application number 202021017897, filed on Apr. 27, 2020. The contents of these applications are hereby incorporated by reference in their entireties.

FIELD OF THE INVENTION

The present invention relates to pharmaceutical composition of Tamsulosin and Solifenacin and process of manufacture thereof. Specifically, the present invention relates to a multiparticulate formulation of Tamsulosin and Solifenacin and process of manufacture thereof. More specifically, the present invention relates to single pellet formulation of Tamsulosin and Solifenacin filled in capsule dosage form.

BACKGROUND OF THE INVENTION

Benign prostatic hyperplasia (BPH) is a common benign disease affecting aging males. BPH can affect patients' health-related quality of life. Irritative voiding symptoms secondary to BPH can lead to sleep disruption, depression, anxiety, increased falls, and sexual problems. Patients with BPH may be presented by irritative and/or obstructive symptoms. Irritative symptoms are in the form of urinary frequency, urgency, nocturia, and urinary incontinence, while obstructive symptoms can be in the form of hesitancy, intermittency, weak stream, or even urinary retention.

Different options of treatment are available to treat BPH like, alpha 1 adrenergic blockers (α1-blockers), 5-α reductase inhibitors (5ARIs) or a combination of the both, anticholinergic agents, β3-adrenoceptor agonists, and phosphodiesterase type-5 inhibitors (PDE5i). Treating benign prostatic hyperplasia with overactive bladder with tamsulosin in combination with solifenacin is more effective than tamsulosin, without significantly increasing adverse reactions.

Tamsulosin hydrochloride is an antagonist of alphalA adrenoceptors in the prostate. Chemically, tamsulosin hydrochloride is (−)-(R)-5-[2-[[2-(o-Ethoxyphenoxy) ethyl] amino]propyl]-2methoxybenzenesulfonamide, monohydrochloride. The empirical formula of tamsulosin hydrochloride is $C_{20}H_{28}N_2O_5S{\cdot}HCl$. The molecular weight of tamsulosin hydrochloride is 444.98. Tamsulosin hydrochloride represented by structural formula (I)

Formula (I)

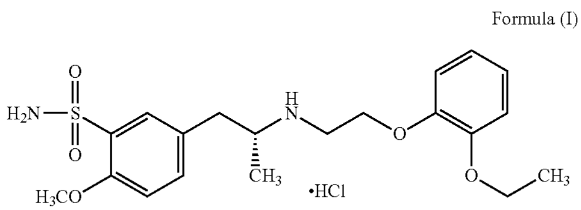 [SMILES: CCOc1ccccc1OCCN[C@H](C)Cc1ccc(OC)c(S(N)(=O)=O)c1 ; Cl]

Tamsulosin hydrochloride is a white crystalline powder that melts with decomposition at approximately 230° C. It is sparingly soluble in water and methanol, slightly soluble in glacial acetic acid and ethanol, and practically insoluble in ether.

Tamsulosin hydrochloride capsules (0.4 mg) approved in the USA under tradename FLOMAX and indicated for the treatment of the signs and symptoms of benign prostatic hyperplasia (BPH).

Solifenacin succinate is a muscarinic receptor antagonist. Chemically, solifenacin succinate is a butanedioic acid compound with (1S)-(3R)-1-azabicyclo[2.2.2]oct-3-yl 3,4-dihydro-1-phenyl-2(1H)-iso-quinolinecarboxylate (1:1). The empirical formula of Solifenacin succinate is $C_{23}H_{26}N_2O_2{\cdot}C_4H_6O_4$. The molecular weight of Solifenacin succinate is 480.55. Solifenacin succinate represented by structural formula (II)

Formula (II)

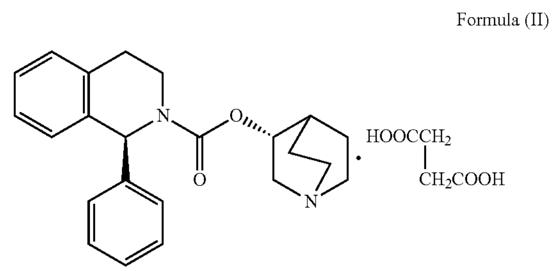

Solifenacin succinate is a white to pale-yellowish-white crystal or crystalline powder. It is freely soluble at room temperature in water, glacial acetic acid, dimethyl sulfoxide, and methanol.

Solifenacin succinate tablet (5 mg &10 mg) are approved in the USA under tradename VESICARE and is indicated for the treatment of adults with overactive bladder with symptoms of urge urinary incontinence, urgency, and urinary frequency.

The combination of Tamsulosin hydrochloride and Solifenacin succinate is approved in European countries under the tradename Vesomni®. The said product is available in the form of modified release tablet (0.4 mg/6 mg) and is indicated in the treatment of moderate to severe storage symptoms (urgency, increased micturition frequency) and voiding symptoms associated with benign prostatic hyperplasia (BPH) in men who are not adequately responding to treatment with monotherapy. The commercially available Vesomni® modified release tablet, administered orally, contains Solifenacin Succinate 6 mg, Tamsulosin HCl 0.4 mg, mannitol (E421), maltose, macrogol 7.000.000, macrogol 8000, magnesium stearate (E470b), butylatedhydroxytoluene (E321), colloidal silica anhydrous (E551), Hypromellose (E464), Iron oxide red (E172).

The marketed Vesomni tablet is double layer tablet consisting one layer of Tamsulosin hydrochloride modified release layer and second layer of Solifenacin succinate immediate release layer.

The European patent publication EP2394648B 1 of Astellas pharma discloses a tablet for oral administration comprising (1) a layer comprising a modified release portion of Tamsulosin or a pharmaceutically acceptable salt thereof and a polymer which forms a hydrogel, and (2) a layer comprising an immediate release portion comprising Solifenacin or a pharmaceutically acceptable salt thereof and at least one hydrophilic substance from the group consisting of D-mannitol, maltose, polyethylene glycol, and polyvinylpyrrolidone.

The Chinese patent publication CN106562968 of Nanjing discloses a kind of sustained release preparation comprising Tamsulosin hydrochloride and Solifenacin succinate, including Tamsulosin hydrochloride slow release layer and Solifenacin immediate release layer, wherein Tamsulosin hydrochloride slow release layer includes Compritol 888 ATO slow-release material and filler, and Solifenacin succinate release layer is made of Solifenacin succinate and diluent and/or lubricant.

The PCT patent publication WO2019076966 of Synthon discloses a pharmaceutical multilayer tablet comprising a controlled release part with Tamsulosin and an immediate release part wherein the immediate release formulation comprises: Solifenacin succinate and a water insoluble diluent in an amount of 50 to 99% w/w relative to the total weight of the immediate release part of the tablet.

A research article entitled "Tamsulosin/solifenacin fixed-dose combination tablet for the treatment of male lower urinary tract symptoms" of author Romancik, Pandian and Drake published in journal Drugs Today 2014, 50(12): 803 discloses tablet of Tamsulosin and Solifenacin fixed-dose combination.

The United States patent publication US20190167612 of Hanmi pharma discloses a pharmaceutical formulation for oral administration with a controlled dissolution rate. The formulation contains Tamsulosin hydrochloride-containing sustained release pellets. The sustained-release pellets include (i) a Tamsulosin hydrochloride, (ii) Hydroxypropyl methylcellulose (HPMC), (iii) an acid-resistant acryl polymer, and (iv) two or more kinds of insoluble diluents. In a specific embodiment, one or more different pharmaceutically active ingredients which may be included in the tamsulosin hydrochloride-containing hard capsule composite formulation are dutasteride, tadalafil, finasteride, solifenacin, or a pharmaceutically acceptable salt thereof, or any mixture thereof. Specifically, for example, formulations such as a hard capsule composite formulation including the tamsulosin-containing sustained-release pellets and a dutasteride soft capsule, a polycap of the tamsulosin-containing sustained-release pellets and a tadalafil-containing tablet or pellet, the tamsulosin-containing sustained-release pellets and a finasteride-containing tablet, or a polycap of the tamsulosin-containing sustained-release pellets and a solifenacin-containing tablet or pellet, etc. may be prepared. The said patent publication US20190167612 does not discloses or teaches single pellet formulation or multiparticulate formulation comprising Tamsulosin and Solifenacin.

The commercially available product or product known in the prior art for Tamsulosin and Solifenacin are in the form of multilayer tablet comprising one layer of Tamsulosin and other layer of Solifenacin. In a multilayer layer tablet, the surface area is limited in comparison to the multiparticulate system. In each multiparticulate system each particles act as separate dosage form unit. In multilayer tablet, presence of hydrophilic polymer affect release of immediate release drug/layer, while in the multiparticulate composition modified release layer comprising polymer comes in contact with gastric media after the outer immediate release layer dissolves or got released.

The manufacturing of the double layer is time consuming and cumbersome process. It may increase the size of tablet; therefore, said tablet possess difficulty in swallowing and lacks patient compliance. Also, these multilayer tablets are prone to dose dumping which results in adverse clinical effect. Further, filing two different type of pellet, granule in capsule possess segregation issue, content uniformity issue, dose dumping issues therefore said products possess adverse clinical effect, not efficacious and lacks patient compliance in the treatment of benign prostatic hyperplasia (BPH) and associated symptoms.

Therefore, there is need in the art to provide composition of Tamsulosin and Solifenacin that is simple, economical, less cumbersome, and easy to swallow. In addition, which avoids issue like dose dumping, segregation issue, content uniformity.

Accordingly, applicant of the present invention invented, multiparticulate composition or single pellet formulation of Tamsulosin and Solifenacin and process of manufacture thereof, which is simple, economical, less cumbersome. In addition, compositions of the present invention avoids issue like dose dumping, segregation issue, content uniformity, difficulty in swallowing and provides efficacy, patient compliance and less adverse clinical effect in the treatment of benign prostatic hyperplasia (BPH) and associated symptoms.

OBJECT OF THE INVENTION

Accordingly, it is an object of the present invention to provide a multiparticulate composition comprising combination of Tamsulosin or a pharmaceutically acceptable salt thereof and Solifenacin or a pharmaceutically acceptable salt thereof.

It is another object of the present invention to provide a multiparticulate composition comprising inner core of Tamsulosin or a pharmaceutically acceptable salt thereof and an outer coating layer of Solifenacin or a pharmaceutically acceptable salt thereof.

It is another object of the present invention to provide a single pellet formulation comprising combination of Tamsulosin or a pharmaceutically acceptable salt thereof and Solifenacin or a pharmaceutically acceptable salt thereof.

It is another object of the present invention to provide a single pellet formulation comprising combination of Tamsulosin or a pharmaceutically acceptable salt thereof and Solifenacin or a pharmaceutically acceptable salt thereof, wherein Tamsulosin is in modified release form and solifenacin is in immediate release form.

It is another object of the present invention to provide a single pellet formulation comprising combination of Tamsulosin or a pharmaceutically acceptable salt thereof and Solifenacin or a pharmaceutically acceptable salt thereof, wherein Tamsulosin in modified release form and solifenacin in immediate release form with one or more pharmaceutical acceptable excipient(s), which is filled in capsule.

It is another object of the present invention to provide a single pellet formulation comprising combination of Tamsulosin and Solifenacin or a pharmaceutically acceptable salt thereof; wherein tamsulosin is in modified release form, solifenacin is in immediate release form used in the treatment of moderate to severe storage symptoms (urgency, increased micturition frequency) and voiding symptoms associated with benign prostatic hyperplasia (BPH) in men who are not adequately responding to treatment with monotherapy.

SUMMARY OF THE INVENTION

The present invention is relates to a multiparticulate composition comprising combination of Tamsulosin or a pharmaceutically acceptable salt thereof and Solifenacin or a pharmaceutically acceptable salt thereof. The present invention also relates to single pellet formulation comprising combination of Tamsulosin or a pharmaceutically acceptable salt thereof and Solifenacin or a pharmaceutically acceptable salt thereof, wherein Tamsulosin in modified release form and solifenacin in immediate release form, which can be fill into capsule.

DETAILED DESCRIPTION OF THE INVENTION

The present invention relates to a multiparticulate composition comprising combination of Tamsulosin or a pharmaceutically acceptable salt thereof and Solifenacin or a pharmaceutically acceptable salt thereof.

The active ingredient Tamsulosin according to present invention may be present in its base form or their hydrochloric acid salt form or may be in the form of their other acid addition salt. Preferably, Tamsulosin is in the form of Tamsulosin hydrochloride salt form.

The active ingredient Solifenacin according to present invention may be present in its base form or their succinic acid salt form or may be in the form of their other acid addition salt. Preferably, Solifenacin is in the form of Solifenacin succinate salt form.

The term "multiparticulate" as used herein means a plurality of discrete or aggregated particles, pellets, beads, granules or mixture thereof irrespective of their size, shape or morphology. The term "multiparticulate" wherein the particulate are pellets, granules, beads, extrudates and seeds or mixture thereof irrespective of their size, shape or morphology.

The multiparticulate multilayer composition according to present invention may be in the form of pellet, granule, bead, spheres or extrudate.

The term formulation or composition according to present invention is intended to encompass at least one active ingredient, and the other inert ingredient(s) (pharmaceutical acceptable excipients). Such compositions, depending upon the context, are also synonymous with "formulation" and "dosage form". These formulations/composition may be prepared in any form, such as solid and liquid dosage form. The solid dosage form can include oral dosage form (powder, tablet, capsule, soft capsule, aqueous medicine, pill, powder, sachet, granule and pellet) and liquid formulation can include solution, suspension, emulsion, syrup, elixirs, etc.

In another embodiment of the present invention is to provide a multiparticulate composition comprising combination of Tamsulosin or a pharmaceutically acceptable salt thereof and Solifenacin or a pharmaceutically acceptable salt thereof along with one or more pharmaceutically acceptable excipient.

The term pharmaceutically acceptable excipient means a pharmacologically inactive component. The excipient(s) that are useful in preparing a pharmaceutical composition are generally safe, non-toxic and are acceptable for human as well as veterinary pharmaceutical use.

In another embodiment of the present invention is to provide a multiparticulate composition comprising combination of Tamsulosin or a pharmaceutically acceptable salt thereof and Solifenacin or a pharmaceutically acceptable salt thereof along with one or more pharmaceutically acceptable excipient; wherein Tamsulosin is in the inner core and solifenacin is in the outer coating.

In another embodiment of the present invention is to provide a multiparticulate composition comprising combination of Tamsulosin or a pharmaceutically acceptable salt thereof and Solifenacin or a pharmaceutically acceptable salt thereof along with one or more pharmaceutically acceptable excipient; wherein Tamsulosin is in the form of modified release and solifenacin is in the form of immediate release.

The term "modified release" as used in describing the present invention means a slower release of the active ingredient than an immediate release dosage form. The term "modified release" can be used interchangeably with "sustained release", "slow release", "controlled release", "extended release" or "long term release.

The multiparticulate composition comprising combination of Tamsulosin or a pharmaceutically acceptable salt thereof and Solifenacin or a pharmaceutically acceptable salt thereof according to present invention contain one or more pharmaceutically acceptable excipient.

The one or more pharmaceutically acceptable excipient according to present invention may be selected from the group consisting of diluents, sustained release (SR) polymers, seal coating polymers, antioxidants, plasticizers, antitacking agents, binders, solubilizer, coloring agent, processing solvents, opacifiers or combination thereof and alike.

The diluent include but not limited to microcrystalline cellulose, lactose monohydrate, mannitol or combination thereof and alike. The most preferably diluent is microcrystalline cellulose. The formulation according to present invention contains from 40 to 95% by weight of diluents.

The sustained release (SR) polymers include but not limited to methacrylic acid copolymer, methacrylic acid ethyl acrylate polymer, Methacrylic acid Copolymer Dispersion (Eudragit L 30D55), Ammonio Methacrylate Copolymer (Type A) (Eudragit RL 100), Ammonio Methacrylate Copolymer (Type B), hypromellose and ethyl cellulose or combination thereof and alike. The most preferably sustained release (SR) polymers is methacrylic acid ethyl acrylate copolymer, Methacrylic acid Copolymer Dispersion (Eudragit L 30D55), Ammonio Methacrylate Copolymer (Type B), Ammonio Methacrylate Copolymer (Type A) (Eudragit RL 100). The formulation according to present invention contains from 5 to 40% by weight of SR polymer. The ratio of Ammonio Methacrylate Copolymer (Type A): Ammonio Methacrylate Copolymer (Type B) according to present invention in the composition is ranging from 1:1 to 1:9.

The term "Seal Coating Polymer" herein refers to as a polymer, used to prevent interaction between two layers. The seal coating polymer(s) is selected from the group consisting of hypromellose, hydroxyl propyl cellulose, methylcellulose, ethyl cellulose or combination thereof and alike. Preferably, seal coating polymer is hypromellose. The formulation according to present invention contains from 2 to 30% by weight of seal coating polymer(s).

The term "Antioxidants" herein refers to those compounds, that inhibit oxidation and added to prevent deterioration due to oxidation process. The antioxidant(s) is selected form the group consisting of butylated Hydroxytoluene, butylated Hydroxyanisole, ascorbic acid, tocopherol, sodium ascorbate, propyl gallate or combination thereof and alike. Preferably, antioxidants are butylated Hydroxytoluene, butylated Hydroxyanisole and propyl gallate. The formulation according to present invention contains from 0.02 to 0.3% by weight of antioxidant(s).

The binder include but not limited to hypromellose, povidone, cellulose or combination thereof and alike. Preferably, binder is povidone. The formulation according to present invention contains from 1 to 20% by weight of binder.

The term "Plasticizer(s)" are used mainly for oral solid dosage forms. Plasticizers are added to the polymers used as film forming agents in order to make the polymer pliable and soft, enhancing the flexibility and plasticity of the films. They are added to these products to reduce the glass transition temperature facilitating the thermal stability of the drug and other ingredients. The plasticizer(s) is selected form the group consisting of Triethyl citrate, triacetin, Polyethylene glycol, Propylene glycol or combination thereof and alike. Preferably, plasticizer is Triethyl citrate. The formulation according to present invention contains from 1-5% by weight of plasticizer(s).

The term "Anti-tacking Agent" is a necessary component in a coating system to prevent tackiness of the dosage forms during the manufacturing process. The anti-tacking agent(s) is selected form the group consisting of talc, silicon dioxide, simethicone, glycerol monosterate or combination thereof and alike. Preferably, anti-tacking agents are talc and silicon dioxide. The pharmaceutical composition contains from 1-10% by weight of anti-tacking agent(s).

The term "Opacifier(s)" used to give more pastel color and increase film coverage. They can provide white coat or mask the color of the tablet/pellet/granule core. These are mostly inorganic material. Opacifier is titanium dioxide, yellow iron oxide. Preferably, opacifier is titanium dioxide. The formulation according to present invention contains from 0.2 to 5% by weight of opacifier.

The term "Processing Solvent(s)" or "Solvent(s)' can serve one or more functions in pharmaceutical manufacture or formulation. Solvents are chemical substances that can dissolve, suspend or extract other materials usually without chemically changing either the solvents or the other materials. Solvents can be organic or inorganic. They used to enhance solubility, taste, anti-microbial effectiveness or stability, to reduce dose volume or to optimize insolubility. Solvents also used to help the final product in achieving proper consistency. The processing solvent(s) is selected form the group consisting of isopropyl alcohol, dichloromethane, Acetone and Purified water or combination thereof and alike.

In another embodiment of the present invention is to provide a multiparticulate, multilayer composition comprising of a) Tamsulosin or a pharmaceutically acceptable salt thereof in Modified or controlled release form as an inner layer
b) Solifenacin or a pharmaceutically acceptable salt thereof in immediate release form as outer layer
c) Optionally one or more protective layer
d) One or more pharmaceutically acceptable excipient
e) multiparticulate multilayer composition has an average diameter of particle ranging from 20 to 1200 um
f) multiparticulate multilayer composition are either
    i) filled in hard or soft gelatin capsule or
    ii) compressed to form a tablet or
    iii) deliver as oral powder or
    iv) converted in suspension dosage form The multiparticulate, multilayer composition according to present invention wherein average diameter of particle in the composition ranging from 20 to 1200 micrometer (μm). The particle size in the composition is measured by Malvern particle size analyzer.

The multiparticulate, multilayer composition according to present invention optionally comprises protective layers. The said protective layers or seal coating layers may be present in the or outside the composition. The multilayer composition According to present invention comprises two or more than two layers in the composition.

The multiparticulate, multilayer composition according to present invention can be filled in to the capsule, or compressed in to tablet or deliver as an oral powder or converted in to the suspension dosage form suitable for human administration.

In another embodiment of the present invention is to provide a multiparticulate composition comprising combination of Tamsulosin or a pharmaceutically acceptable salt thereof and Solifenacin or a pharmaceutically acceptable salt thereof along with one or more pharmaceutically acceptable excipient in the form of single pellet formulation.

In another embodiment of the present invention is to provide single pellet formulation comprising combination of Tamsulosin or a pharmaceutically acceptable salt thereof and Solifenacin or a pharmaceutically acceptable salt thereof.

In another embodiment of the present invention is to provide single pellet formulation comprising combination of Tamsulosin or a pharmaceutically acceptable salt thereof and Solifenacin or a pharmaceutically acceptable salt thereof; wherein tamsulosin is in the core and solifenacin is in the outer coating In another embodiment of the present invention is to provide single pellet formulation comprising combination of Tamsulosin or a pharmaceutically acceptable salt thereof and Solifenacin or a pharmaceutically acceptable salt thereof; wherein tamsulosin is in the modified release form and solifenacin is in the immediate release form.

In another embodiment of the present invention is to provide single pellet formulation comprising combination of Tamsulosin or a pharmaceutically acceptable salt thereof and Solifenacin or a pharmaceutically acceptable salt thereof; wherein tamsulosin is in the modified release form, which is in the core of pellet, and solifenacin is in the immediate release form; which is in the outer coating.

In another embodiment of the present invention is to provide a process of manufacturing multiparticulate composition comprising combination of Tamsulosin or a pharmaceutically acceptable salt thereof and Solifenacin or a pharmaceutically acceptable salt thereof along with one or more pharmaceutically acceptable excipient.

In another embodiment of the present invention is to provide a process of manufacturing single pellet formulation comprising combination of Tamsulosin or a pharmaceutically acceptable salt thereof and Solifenacin or a pharmaceutically acceptable salt thereof along with one or more pharmaceutically acceptable excipient.

In another embodiment of the present invention is to provide a process of manufacturing single pellet formulation comprising the step of i) Preparing the core of Tamsulosin along with one or more pharmaceutically acceptable excipient.
ii) Drug Loading or coating the solifenacin over the tamsulosin core prepared in step
i) along with one more pharmaceutically acceptable solvent.

In another embodiment of the present invention is to provide a process of manufacturing single pellet formulation comprising the step of i) Mixing Tamsulosin along with one or more pharmaceutically acceptable excipient to form granules.
ii) Spheronize the said granule in spheronizer to form the pellet.
iii) Drug Loading or coating the solifenacin over the tamsulosin pellet prepared in step ii) along with one more pharmaceutically acceptable solvent.

In another embodiment of the present invention is to provide a process of manufacturing single pellet formulation comprising the step of i) Mixing Tamsulosin along with one or more pharmaceutically acceptable excipient to form granules. Spheronize the said granule in spheronizer to form the pellet.
ii) Coating the pellet prepared in step i) by sustained release coating.
iii) Drug Loading or coating the solifenacin over the sustained release coated pellet prepared in step ii) along with one more pharmaceutically acceptable solvent.

In another embodiment of the present invention is to provide a process of manufacturing single pellet formulation comprising the step of i) Mixing Tamsulosin along with one or more pharmaceutically acceptable excipient to form granules. Spheronize the said granule in spheronizer to form the pellet.

ii) Seal coating the pellet prepared in step i) by using seal coating agent.
iii) Coating the seal coated pellet prepared in step ii) by sustained release coating.
iv) Drug Loading or coating the solifenacin over the sustained release coated pellet prepared in step iii) along with one more pharmaceutically acceptable solvent.

In another embodiment of the present invention is to provide a process of manufacturing single pellet formulation comprising the step of i) Mixing Tamsulosin along with one or more pharmaceutically acceptable excipient to form granules. Spheronize the said granule in spheronizer to form the pellet.
ii) Seal coating the pellet prepared in step i) by using seal coating agent.
iii) Coating the seal coated pellet prepared in step ii) by sustained release coating.
iv) Seal coating the sustained release coated pellet prepared in step iii) by using seal coating agent.
v) Drug Loading or coating the solifenacin over the seal coated pellet prepared in step iv) along with one more pharmaceutically acceptable solvent.

In another embodiment of the present invention is to provide a process of manufacturing multiparticulate composition comprising combination of Tamsulosin or a pharmaceutically acceptable salt thereof and Solifenacin or a pharmaceutically acceptable salt thereof along with one or more pharmaceutically acceptable excipient; wherein core of the formulation may be in the form of pellet, granule, bead, sphere, extrudate. The said core contain Tamsulosin or a pharmaceutically acceptable salt in the form of modified release and immediate release solifenacin over the said core.

In another embodiment of the present invention is to provide multiparticulate composition comprising combination of Tamsulosin or a pharmaceutically acceptable salt thereof and Solifenacin or a pharmaceutically acceptable salt thereof along with one or more pharmaceutically acceptable excipient may be in the form of pellet, granule, bead, sphere, extrudate. The said pellet, granule, bead, sphere, or extrudate may be filled in to the capsule, or converted in to the pharmaceutical dosage form for administration to the patient.

In another embodiment of the present invention is to provide multiparticulate composition, wherein concentration of Tamsulosin or a pharmaceutically acceptable salt thereof and Solifenacin or a pharmaceutically acceptable salt thereof, one or more pharmaceutically acceptable excipient is optimized in such way that, formulation provides desired release in the treatment of benign prostatic hyperplasia (BPH) and associated symptoms.

The multiparticulate composition comprising combination of Tamsulosin or a pharmaceutically acceptable salt thereof and Solifenacin or a pharmaceutically acceptable salt thereof according to present invention provides similar in-vitro drug release profile as the of commercially available Vesomni® modified release tablet; therefore multiparticulate formulation according to present invention found to be in the compliance.

In another embodiment of the present invention is to provide multiparticulate composition comprising Tamsulosin and Solifenacin wherein, dissolution rate of Tamsulosin from composition is not more than of 40% after 4 hours and not more than of 80% in 12 hours. The dissolution measured in vitro in USP Apparatus Type 2 (Paddle) using pH 6.8-phosphate buffer of 900 mL, at 100 rpm.

In another embodiment of the present invention is to provide, multiparticulate, multilayer composition were subjected to in vivo studies in human produces a plasma profile characterized by a $C_{max}$ for Tamsulosin between 3.5 ng/ml to 12 ng/ml and $C_{max}$ for Solifenacin between 12 ng/ml to 35 ng/ml.

$C_{max}$ is a maximum concentration that a drug achieves in tested area after the drug has been administrated and prior to the administration of a second dose. $C_{max}$ is the opposite of $C_{min}$, which is the minimum concentration that a drug achieves after dosing. $T_{max}$ is the term used in pharmacokinetics to describe the time at which the $C_{max}$ is observed.

Bioequivalence Summary for Multiparticulate Composition of Comprising Tamsulosin and Solifenacin:

The ratio of geometric LS means with corresponding 90% confidence interval calculated from the exponential of the difference between the Test and Reference product for the ln-transformed parameters $C_{max}$ and AUCO-t (tamsulosin) or AUC 0-24 (solifenacin) were all within 80.00 to 125.00% bioequivalence range for fasted BE study.

The 90% confidence intervals of the T/R ratios shown in the following table:

TABLE 1

| Bioequivalence Criteria Solifenacin | | | |
|---|---|---|---|
| PHARMACOKINETIC PARAMETERS | TEST/ REFERENCE RATIO | 90% CONFIDENCE INTERVAL FOR TEST Vs REFERENCE | INTER SUBJECT CV |
| LN_Cmax | 100.92% | (89.3% TO 111.8%) | 18.4% |
| LN_AUC0-24 | 98.15% | (92.3% TO 112.2%) | 13.7% |

TABLE 2

| Bioequivalence Criteria Tamsulosin | | | |
|---|---|---|---|
| PHARMACOKINETIC PARAMETERS | TEST/ REFERENCE RATIO | 90% CONFIDENCE INTERVAL FOR TEST Vs REFERENCE | INTER SUBJECT CV |
| LN_Cmax | 104.15% | (90.5% TO 108.7%) | 20.1% |
| LN_AUC0-t | 100.42% | (88.10% TO 118.1%) | 24.3% |

The multiparticulate composition comprising combination of Tamsulosin or a pharmaceutically 20 acceptable salt thereof and Solifenacin or a pharmaceutically acceptable salt thereof according to present invention were loaded for stability study at condition of 40° C./75% RH, 30° C./75% RH, 25° C./60% RH as per ICH guideline. After stability study, in-vitro drug release profile, assay, related substances and other parameters found to be in the compliance.

Accordingly, multiparticulate composition of the present invention found to be stable, which is simple, economical, less cumbersome to manufacture and easy to swallow. In addition, which avoids issue like dose dumping, segregation issue, content uniformity and provides efficacy, patient compliance and less adverse clinical effect in the treatment of benign prostatic hyperplasia (BPH) and associated symptoms.

The multiparticulate composition of the present invention packaged in suitable airtight containers and moisture proof packs. The pharmaceutical composition of the present invention preferably packaged in to the strip, blister, bottle or sachet.

EXAMPLE

The following Examples are provided solely for illustrative purposes and are not meant to limit the invention in any way.

TABLE 3

Composition of Tamsulosin and Solifenacin pellet:

| Sr. No. | Ingredients | % (Range) |
|---|---|---|
| 1. | Tamsulosin HCl | 0.1-0.5 |
| 2. | Microcrystalline Cellulose PH 101 | 40-95 |
| 3. | Methacrylic acid Copolymer Dispersion (Eudragit L 30D55) | 5-15 |
| 4. | Ammonio Methacrylate Copolymer, Type A | 5-20 |
| 5. | Ammonio Methacrylate Copolymer, Type B | 5-20 |
| 6. | Hypromellose 5 cps | 5-20 |
| 7. | Purified Talc | 2-10 |
| 8. | Ammonio Methacrylate Copolymer (Type A) (Eudragit RL 100) | 2-8 |
| 9. | Ethyl cellulose | 2-8 |
| 10. | Triethyl Citrate | 1-5 |
| 11. | Butylated Hydroxytoluene | 0.02-0.2 |
| 12. | Solifenacin Succinate | 1-5 |
| 13. | Isopropyl alcohol:DCM | q.s. |
| 14. | Purified Water | q.s. |

q.s.—Quantity Sufficient

Brief Manufacturing Process:

Stage I: Dry Mix/Granulation

Dry mix drug Tamsulosin, Diluent (i.e. Microcrystalline Cellulose PH101), blend for suitable time, and granulate with purified water and optional Release Modifying Agent (i.e. Methacrylic acid copolymer dispersion Eudragit L-30 D55).

Stage II: Extrusion/Spheronization

Mass obtained was Extruded using suitable screen (1.2 mm) and spheronized further into pellets. Spheronized pellets dried in FLP/FBD and sifted through suitable screen.

Stage III: Seal Coating 1

Obtained Tamsulosin pellets subjected to Seal coating in FBC using solution of Hypromellose 5 cps, Purified Talc in Purified Water.

Stage IV: Sustained Release Coating

Tamsulosin seal coated pellets were enrobed in sustain release coat in FBC using one or more sustain release polymers like Methacrylic acid copolymer dispersion Eudragit L-30 D55, Ammonio Methacrylate copolymer Type A, Ammonio Methacrylate copolymer Type B and Ethyl cellulose.

Stage V: Seal Coating 2

Tamsulosin SR pellets were sprayed with solution containing Hypromellose 5 cps, Antioxidant (Butylated Hydroxy Toluene or Butylated Hydroxy anisole), Purified Talc and Triethyl citrate in solvent(Mixture of Isopropyl Alcohol and Methylene Chloride) to obtain a sub coat over Tamsulosin SR pellets.

Stage VI: Drug Layering/Loading:

Drug solution of Solifenacin Succinate was prepared by dispersing Solifenacin Succinate, Hypromellose 50 cps and Antioxidant (Butylated Hydroxyl Toluene or Butylated Hydroxy anisole) in Isopropyl Alcohol and this solution was applied uniformly over Sub coated Tamsulosin SR pellets to form Solifenacin layer.

Stage VII: Final Seal Coating:

In order to Protect Solifenacin layer, A protective layer of Hypromellose 5 cps, Antioxidant (Butylated Hydroxyl Toluene or Butylated Hydroxy anisole), Purified Talc and Triethyl citrate in solvent(Mixture of Isopropyl Alcohol and Methylene Chloride) was applied. Obtained pellets were dried using FBC.

Different trials were taken using optimized concentration of polymers and coating layer optimization were done to match in-vitro dissolution profile for Tamsulosin SR layer and Solifenacin Succinate IR layer with reference product Vesomm, from trials most promising batch with different strategy close to reference product were selected for further study. List of examples with composition has been enlisted below:

Examples 1 to 5

TABLE 4

| Examples of Pellet | | | | | |
|---|---|---|---|---|---|
| Ingredient | Example1 | Example-2 | Example3 | Example4 | Example 5 |
| Tamsulosin HCl | 0.1-0.5 | 0.1-0.5 | 0.1-0.5 | 0.1-0.5 | 0.1-0.5 |
| Solifenacin Succinate | 6 | 6 | 6 | 6 | 6 |
| Microcrysatlline Cellulose PH101 | 242.1 | 229.6 | 250.1 | 250.1 | 250.1 |
| Methacrylic acid copolymer dispersion Eudragit L-30 D55 | 25 | . . . | . . . | . . . | . . . |
| Ammonio Methacrylate copolymer Type A | . . . | 25 | 20 | 15 | 5 |
| Ammonio Methacrylate copolymer Type B | . . . | 25 | 30 | 35 | 45 |
| Hypromellose 5 cps | 28.3 | 28.8 | 28.8 | 28.8 | 28.8 |
| Ammonio Methacrylate copolymer (Type A) Eudragit RL 100 | 22 | 10 | . . . | . . . | . . . |
| Ethylcellulose | 11 | 10 | . . . | . . . | . . . |
| Triethyl citrtae | 5 | 5.5 | 5.5 | 5.5 | 5.5 |
| Butylated Hydroxy anisol | . . . | . . . | 0.5 | 0.5 | 0.5 |
| Butylated Hydroxytoulene | 0.7 | 0.7 | 0.7 | 0.7 | 0.7 |
| Purified Talc | 8.5 | 8 | 8 | 8 | 8 |
| purified water | Qs | Qs | Qs | Qs | Qs |
| IPA:DCM | Qs | Qs | Qs | Qs | Qs |
| Total | 350 | 350 | 350 | 350 | 350 |

Dissolution Profile for Examples 1 to 5

Tamsulosin:

Dissolution media for Tamsulosin HCl: pH 6.8 Phosphate buffer, 900 ml, 100 RPM, USP 2 apparatus (paddle) with sinker, Temperature 37±0.5° C.

TABLE 5

| Dissolution results for Tamsulosin HCl SR: | | | | | | |
|---|---|---|---|---|---|---|
| Time (Hr) | Vesomni | Example-1 | Example-2 | Example-3 | Example-4 | Example-5 |
| 2 | 16 | 6 | 16 | 23 | 21 | 18 |
| 4 | 26 | 16 | 34 | 32 | 30 | 28 |
| 6 | 39 | 26 | 47 | 48 | 48 | 45 |
| 8 | 48 | 37 | 56 | 59 | 58 | 55 |
| 10 | 53 | 49 | 63 | 67 | 64 | 58 |
| 12 | 68 | 63 | 70 | 77 | 75 | 74 |
| 18 | 85 | 90 | 79 | 93 | 91 | 90 |
| 20 | 90 | 92 | 82 | 96 | 95 | 93 |
| 24 | 93 | 95 | 85 | 97 | 96 | 96 |

Solifenacin:

Dissolution media for Solifenacin succinate: Water, 900 ml, 100 RPM, USP 2 apparatus (paddle) with sinker, Temperature 37±0.5° C.

TABLE 6

| Dissolution result of Solifenacin Succinate: | | | | | | |
|---|---|---|---|---|---|---|
| Time (Mi) | Vesomni | Example-1 | Example-2 | Example-3 | Example-4 | Example-5 |
| 15 | 86 | 65 | 96 | 88 | 90 | 89 |
| 30 | 87 | 72 | 98 | 89 | 91 | 92 |
| 45 | 90 | 74 | 100 | 91 | 95 | 93 |
| 60 | 91 | 76 | 100 | 95 | 96 | 95 |

Conclusion: As per above result, the dissolution of the test product, example 1 to 5 were found to be similar to reference product Vesomni.

Stability Data (For Example 5)

TABLE 7

| Stability condition: 40° C./75% RH (1, 3, 6 Month): | | | | | | | | | | | | | |
|---|---|---|---|---|---|---|---|---|---|---|---|---|---|
| | | | | | | Dissolution (%) of | Related Substances | | | | | |
| | | | Dissolution | | | Solifenacin | Tamsulosin HCl | | | Solifenacin Succinate | | |
| | Assay | | (%) of Tamsulosin HCl 900 ml, Phosphate | | | Succinate 900 ml, 0.1N HCl, pH 1.2, | Impurity | Highest Unknown Individual | Total | Impurity | Highest Unknown Individual | Total |
| Tests Condition/ | Tamsulosin HCL | Solifenacin Succinate | buffer pH 6.8, Paddle, 100 RPM | | | paddle, 100 RPM | H NMT | Impurity NMT | impurity NMT | I NMT | Impurity NMT | impurity NMT |
| Interval | Limit: 95.0-105.0% | | 2 hr | 12 hr | 24 hr | 45 mins | 1.0% | 1.0% | 2.0 | 0.8% | 0.33% | 2.0 |
| Initial | 97.6 | 99.5 | 5 | 62 | 95 | 93 | ND | ND | ND | 0.29 | 0.12 | 0.41 |
| 40° C./75% RH_1 M | 99.6 | 100.3 | 6 | 65 | 97 | 92 | ND | ND | ND | 0.38 | 0.25 | 0.63 |
| 40° C./75% RH_3 M | 96.1 | 97.0 | 3 | 55 | 90 | 90 | ND | ND | ND | 0.55 | 0.31 | 0.86 |
| 40° C./75% RH_6 M | 96.4 | 95.0 | 4 | 55 | 87 | 90 | ND | ND | ND | 0.49 | 0.28 | 0.77 |

TABLE 8

| Stability condition: 30° C./75% RH (1, 3, 6 Month): | | | | | | | | | | | | | |
|---|---|---|---|---|---|---|---|---|---|---|---|---|---|
| | | | | | | Dissolution (%) of | Related Substances | | | | | |
| | | | Dissolution | | | Solifenacin | Tamsulosin HCl | | | Solifenacin Succinate | | |
| | Assay | | (%) of Tamsulosin HCl 900 ml, Phosphate | | | Succinate 900 ml, 0.1N HCl, pH 1.2, | Impurity | Highest Unknown Individual | Total | Impurity | Highest Unknown Individual | Total |
| Tests Condition/ | Tamsulosin HCL | Solifenacin Succinate | buffer pH 6.8, Paddle, 100 RPM | | | paddle, 100 RPM | H NMT | Impurity NMT | impurity NMT | I NMT | Impurity NMT | impurity NMT |
| Interval | Limit: 95.0-105.0% | | 2 hr | 12 hr | 24 hr | 45 mins | 1.0% | 1.0% | 2.0 | 0.8% | 0.33% | 2.0 |
| 30° C./75% RH_1 M | 100.3 | 98.9 | 6 | 61 | 93 | 99 | ND | ND | ND | 0.34 | 0.19 | 0.53 |
| 30° C./75% RH_3 M | 96.6 | 96.8 | 4 | 58 | 95 | 99 | ND | ND | ND | 0.45 | 0.32 | 0.77 |
| 30° C./75% RH_6 M | 96.9 | 97.0 | 4 | 54 | 91 | 100 | ND | ND | ND | 0.41 | 0.34 | 0.75 |

TABLE 9

| Stability condition: 25° C./60% RH (1, 3, 6 Month): | | | | | | | | | | | | | |
|---|---|---|---|---|---|---|---|---|---|---|---|---|---|
| | | | | | | Dissolution (%) of | Related Substances | | | | | |
| | | | Dissolution | | | Solifenacin | Tamsulosin HCl | | | Solifenacin Succinate | | |
| | Assay | | (%) of Tamsulosin HCl 900 ml, Phosphate | | | Succinate 900 ml, 0.1N HCl, pH 1.2, | Impurity | Highest Unknown Individual | Total | Impurity | Highest Unknown Individual | Total |
| Tests Condition/ | Tamsulosin HCL | Solifenacin Succinate | buffer pH 6.8, Paddle, 100 RPM | | | paddle, 100 RPM | H NMT | Impurity NMT | impurity NMT | I NMT | Impurity NMT | impurity NMT |
| Interval | Limit: 95.0-105.0% | | 2 hr | 12 hr | 24 hr | 45 mins | 1.0% | 1.0% | 2.0 | 0.8% | 0.33% | 2.0 |
| 25° C./60% RH_1 M | 102.1 | 99.1 | 5 | 62 | 95 | 96 | ND | ND | ND | 0.33 | 0.16 | 0.49 |

TABLE 9-continued

| Stability condition: 25° C./60% RH (1, 3, 6 Month): | | | | | | | | | | | | |
|---|---|---|---|---|---|---|---|---|---|---|---|---|
| | | | | | | Dissolution (%) of | Related Substances | | | | | |
| | | | Dissolution | | | Solifenacin | Tamsulosin HCl | | | Solifenacin Succinate | | |
| | Assay | | (%) of Tamsulosin HCl 900 ml, Phosphate | | | Succinate 900 ml, 0.1N HCl, pH 1.2, | Impurity | Highest Unknown Individual | Total | Impurity | Highest Unknown Individual | Total |
| Tests Condition/ | Tamsulosin HCL | Solifenacin Succinate | buffer pH 6.8, Paddle, 100 RPM | | | paddle, 100 RPM | H NMT | Impurity NMT | impurity NMT | I NMT | Impurity NMT | impurity NMT |
| Interval | Limit: 95.0-105.0% | | 2 hr | 12 hr | 24 hr | 45 mins | 1.0% | 1.0% | 2.0 | 0.8% | 0.33% | 2.0 |
| 25° C./60% RH_3 M | 97.3 | 97.2 | 4 | 58 | 93 | 97 | ND | ND | ND | 0.42 | 0.26 | 0.68 |
| 25° C./60% RH_6 M | 96.5 | 98.8 | 6 | 62 | 92 | 95 | ND | ND | ND | 0.37 | 0.12 | 0.49 |

Examples 6 to 8

TABLE 10

| Examples of Soft gelatin capsule | | | |
|---|---|---|---|
| Ingredients | Example-6 | Example-7 | Example-8 |
| Tamsulosin & Solifinacin Pellets | 350 | 350 | 350 |
| Mono-di-glycerides of caprylic/capric acid | 80 | 100 | 120 |
| Butylhydroxytoluene | 0.8 | 0.8 | 0.8 |
| Soft Capsules | . . . | . . . | . . . |
| Gelatin | 185.2 | 195.2 | 196.2 |
| Glycerol | 46 | 46 | 46 |
| Titanium dioxide (E171) | 22 | 22 | 22 |
| Iron Oxide Yellow (El72) | 11 | 11 | 11 |
| Triglycerides, medium chain | 5 | 5 | 5 |
| Lecithin (may contain soya oil) | 10 | 10 | 10 |
| Total | 710 | 740 | 761 |

Examples 9 to 13

TABLE 11

| Examples of MUPS | | | | | |
|---|---|---|---|---|---|
| Ingredients | Example-9 | Example-10 | Example-11 | Example-12 | Example-13 |
| Tamsulosin & Solifinacin Pellets | 350 | 350 | 350 | 350 | 350 |
| Cushioning agent | | | | | |
| Microcrysatlline Cellulose (Ceolus-KG 1000) | 100 | 100 | 100 | 100 | 100 |
| Colloidal Anhydrous Silica (Aerosil 200) | 15 | 15 | 15 | 15 | 15 |
| Polyethylene Glycol 6000 | 20 | 30 | 40 | 50 | 60 |
| Total | 485 | 495 | 505 | 515 | 525 |

Examples 14 to 18

TABLE 12

| Examples of Oral Suspension | | | | | |
|---|---|---|---|---|---|
| Ingredients | Example-14 | Example-15 | Example-16 | Example-17 | Example-18 |
| Pellets | | | | | |
| Tamsulosin & Solifinacin Pellets | 350 | 350 | 350 | 350 | 350 |
| Oral Suspension | | | | | |
| Xanthan gum (Xantural-75) | 10 | 15 | 20 | 10 | 10 |
| Guar Gum | 30 | 40 | 45 | 45 | 50 |
| Sucrose | 145 | 130 | 120 | 130 | 125 |
| Colloidal anhydrous Silica | 5 | 5 | 5 | 5 | 5 |
| Banana Flavour | 10 | 10 | 10 | 10 | 10 |
| Total | 550 | 550 | 550 | 550 | 550 |

We claim:

1. A composition comprising:

a plurality of discrete or aggregate particles acting as a separate dosage form unit, wherein each particle comprises:

a) an inner layer comprising tamsulosin or a pharmaceutically acceptable salt thereof, and diluents, wherein the inner layer is in a modified release form;

b) a first seal coat over the inner layer, wherein the first seal coat comprises Hypromellose 5 cps;

c) a sustained-release coating over the first seal coat, wherein the sustained release coating comprises modified-release polymers;

d) a second seal coat over the sustained-release coating, wherein the first second seal coat comprises Hypromellose 5 cps, and antioxidants;

e) an outer layer over the second seal coat, wherein the outer layer comprises solifenacin or a pharmaceutically acceptable salt thereof, Hypromellose 5 cps, and antioxidants, wherein the outer layer is in an immediate release form; and f) one or more protective layers configured to protect the outer layer, wherein the one or more protective layers comprise Hypromellose 5 cps, and butylated hydroxyl toluene;

wherein each of the plurality of the discrete or aggregate particles has an average particle diameter ranging from 20 to 1200 μm.

2. The composition according to claim 1, wherein the composition is in the form of a granule, or an extrudate.

3. The composition according to claim 1, wherein the composition is in the form of a pellet.

4. The composition according to claim 1, wherein the modified-release polymers are selected from the group consisting of methacrylic acid copolymer, methacrylic acid ethyl acrylate polymer, ammonio methacrylate copolymer (Type A), ammonio methacrylate copolymer (Type B), ethyl cellulose, and a combination thereof.

5. The composition according to claim 4, wherein ammonio methacrylate copolymer (Type A), and ammonio methacrylate copolymer (Type B) are in a ratio ranging from 1:1 to 1:9.

6. The composition according to claim 1, wherein the antioxidants are selected from the group consisting of butylated hydroxytoluene, butylated hydroxyanisole, ascorbic acid, tocopherol, sodium ascorbate, propyl gallate, and a combination thereof.

7. The composition according to claim 1, wherein the dissolution rate of tamsulosin from the composition is less than 40% within 4 hours and less than 80% within 12 hours, when measured in vitro in an USP Apparatus Type 2 (Paddle) using 900 mL of pH 6.8 buffer, at 100 rpm.

8. The composition according to claim 1, wherein the composition is a hard gelatin capsule, a soft gelatin capsule, a powder, a suspension, or a tablet.

9. The composition according to claim 1, wherein the diluents are selected from the group consisting of microcrystalline cellulose, lactose monohydrate, mannitol, and a combination thereof.

10. The composition according to claim 9, wherein the diluent is microcrystalline cellulose.

11. The composition according to claim 9, wherein the composition comprises 40 to 95% by weight of diluent.

12. The composition according to claim 1, wherein the protective layer further comprises purified talc, and triethyl citrate in a solvent.

13. The composition according to claim 12, wherein the solvent is a mixture of isopropyl alcohol and methylene chloride.

14. A process of manufacturing a composition, the process comprising the step of:

i) mixing tamsulosin or a pharmaceutically acceptable salt thereof with diluents to obtain a mixture, and spheronizing the mixture in a spheronizer to form an inner layer;

ii) seal coating the inner layer prepared in step i) by using Hypromellose 5 cps to obtain a first seal coat;

iii) coating the first seal coat prepared in step ii) by modified-release polymers to obtain a sustained-release coating;

iv) seal coating the sustained-release coating by using Hypromellose 5 cps, and antioxidants to obtain a second seal coat;

v) coating solifenacin or a pharmaceutically acceptable salt thereof over the second seal coat prepared in step iv) along with Hypromellose 5 cps, and antioxidants to obtain an outer layer, wherein the outer layer is in an immediate release form;

vi) coating the outer layer with one or more protective layers, wherein the one or more protective layers comprise Hypromellose 5 cps, and butylated hydroxyl toluene, wherein each of the plurality of the discrete or aggregate particles has an average particle diameter ranging from 20 to 1200 μm, and wherein each of the plurality of the discrete or aggregate particles acts as a separate dosage form unit.

* * * * *